(12) United States Patent
Zhang et al.

(10) Patent No.: US 11,055,873 B2
(45) Date of Patent: Jul. 6, 2021

(54) COMPOSITE IMAGE GENERATION SYSTEM AND POSITION INFORMATION CORRECTION SYSTEM

(71) Applicant: TCC Media Lab CO., LTD., Chofu (JP)

(72) Inventors: Bo Zhang, Tokyo (JP); Kui Chen, Tokyo (JP); Weiyi Cai, Tokyo (JP); Shunichi Tano, Tokyo (JP)

(73) Assignee: TCC MEDIA LAB CO., LTD, Tokyo (JP)

(*) Notice: Subject to any disclaimer, the term of this patent is extended or adjusted under 35 U.S.C. 154(b) by 0 days.

(21) Appl. No.: 17/045,874

(22) PCT Filed: Feb. 1, 2019

(86) PCT No.: PCT/JP2019/003744
§ 371 (c)(1),
(2) Date: Oct. 7, 2020

(87) PCT Pub. No.: WO2020/157984
PCT Pub. Date: Aug. 6, 2020

(65) Prior Publication Data
US 2021/0142509 A1 May 13, 2021

(51) Int. Cl.
G06T 7/73 (2017.01)
G06T 19/00 (2011.01)
(Continued)

(52) U.S. Cl.
CPC .............. G06T 7/73 (2017.01); A61B 5/0035 (2013.01); A61B 5/0077 (2013.01); A61B 5/064 (2013.01);
(Continued)

(58) Field of Classification Search
CPC ......... G06T 7/73; G06T 7/246; G06T 19/006; G06T 2207/30004; G06T 2207/30204;
(Continued)

(56) References Cited

U.S. PATENT DOCUMENTS 9,019,349 B2 * 4/2015 Richardson ........ H04N 5/23203
348/47
2015/0109458 A1 4/2015 Lee
(Continued)

FOREIGN PATENT DOCUMENTS

JP 2002-533721 A 10/2002
JP 5410629 B1 2/2014
(Continued)

OTHER PUBLICATIONS

Dorfmüller-Ulhaas, Klaus. "Robust optical user motion tracking using a kalman filter." (2007). (Year: 2007).*
(Continued)

Primary Examiner — Pinalben Patel
(74) Attorney, Agent, or Firm — Westerman, Hattori, Daniels & Adrian, LLP

(57) ABSTRACT

A composite image generation system comprises: a position information detection device 14 that detects position information about a predetermined spot in a real space; and a processing device 16 that generates a composite image in which a separately acquired superimposed image is overlaid onto a desired region in a camera image of the real space captured by a movably placed video camera 18, based on the position information from the position information detection device 14. The processing device 16 includes a position information specifying means 35 that adjusts a detection result from the position information detection device 14 to specify position information about a probe 19 used when superimposing the superimposed image onto the desired (Continued)

region. The position information specifying means 35 comprises a recognition state determination unit 46 that determines a recognition state of a probe marker 24A by the video camera 18, a used information selection unit 47 that selects which of detection results from an optical tracking means 21 and a non-optical tracking means 22 is to use according to the recognition state, and an output position information decision unit 48 that decides output position information necessary to generate a composite image according to the selected position information.

9 Claims, 2 Drawing Sheets

(51) Int. Cl.
| | | |
|---|---|---|
| *H04N 5/272* | (2006.01) | |
| *G01B 7/004* | (2006.01) | |
| *G01P 15/18* | (2013.01) | |
| *A61B 8/00* | (2006.01) | |
| *A61B 8/08* | (2006.01) | |
| *A61B 5/00* | (2006.01) | |
| *A61B 5/06* | (2006.01) | |
| *G06T 7/246* | (2017.01) | |

(52) U.S. Cl.
CPC ............ *A61B 8/463* (2013.01); *A61B 8/5261* (2013.01); *G01B 7/004* (2013.01); *G01P 15/18* (2013.01); *G06T 7/246* (2017.01); *G06T 19/006* (2013.01); *H04N 5/272* (2013.01); *A61B 2562/0219* (2013.01); *A61B 2562/0223* (2013.01); *G06T 2207/30004* (2013.01); *G06T 2207/30204* (2013.01); *G06T 2210/41* (2013.01)

(58) Field of Classification Search
CPC . G06T 2210/41; A61B 5/0035; A61B 5/0077; A61B 5/064; A61B 8/463; A61B 8/5261; A61B 2562/0219; A61B 2562/0223; G01B 7/004; G01P 15/18; H04N 5/272
See application file for complete search history.

(56) References Cited

U.S. PATENT DOCUMENTS

| | | | |
|---|---|---|---|
| 2015/0366527 A1* | 12/2015 | Yu ..................... | G01R 33/56509 382/131 |
| 2021/0049914 A1* | 2/2021 | Dalan .................... | G08G 5/006 |

FOREIGN PATENT DOCUMENTS

| | | |
|---|---|---|
| JP | 2016-202351 A | 12/2016 |
| JP | 6095032 B1 | 3/2017 |
| JP | 2017-153827 A | 9/2017 |

OTHER PUBLICATIONS

Amin, Dhiraj, and Sharvari Govilkar. "Comparative study of augmented reality SDKs." International Journal on Computational Science & Applications 5.1 (2015): 11-26. (Year: 2015).*
Grimson, W. Eric L., et al. "An automatic registration method for frameless stereotaxy, image guided surgery, and enhanced reality visualization." IEEE Transactions on medical imaging 15.2 (1996): 129-140. (Year: 1996).*
International Search Report dated Mar. 19, 2019, issued in counterpart International Application No. PCT/JP2019/003744. (1 page).
Decision to Grant a Patent dated Jan. 29, 2020, issued in counterpart of Japanese Patent Application No. 2019-506535, with English Translation. (5 pages).

* cited by examiner

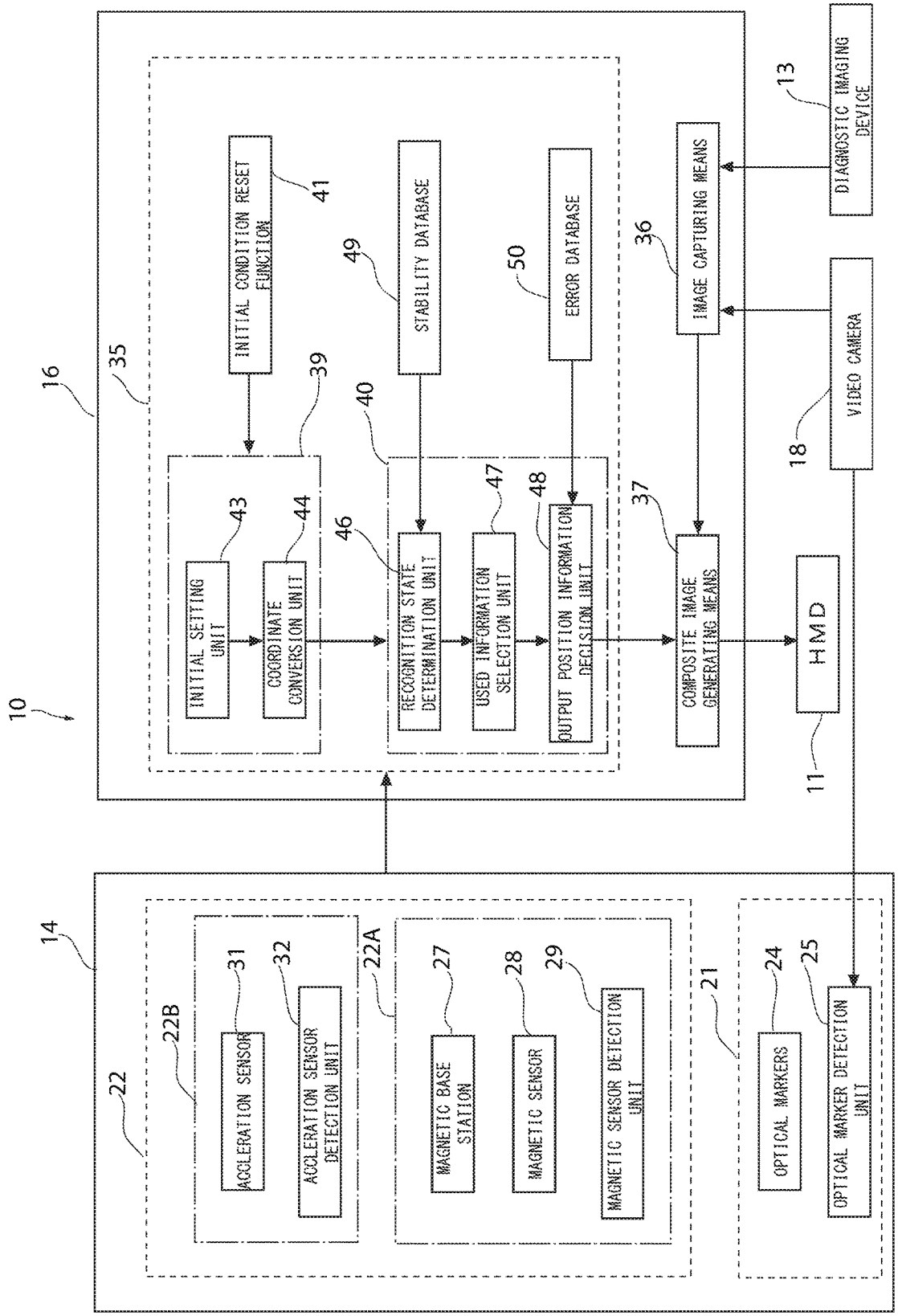

COMPOSITE IMAGE GENERATION SYSTEM AND POSITION INFORMATION CORRECTION SYSTEM

TECHNICAL FIELD

The present invention relates to a composite image generation system that overlays a superimposed image acquired elsewhere onto a partial region of an image capturing a real space of the outside world, and also to a position information correction system used for the composite image generation system.

BACKGROUND ART

Recently, the application of virtual reality (VR) and augmented reality (AR) technologies to various other fields is being investigated. As an application of AR technology to the medical field, research is being conducted on a system that supports applications such as medical education and minimally invasive surgery by using a head-mounted display (HMD) of the video see-through type, which allows a user to see a predetermined superimposed image overlaid onto a camera image capturing a real space in the outside world. A known example of such a system is the support system described in Patent Literature 1, in which a doctor wears an HMD when performing a procedure such as paracentesis, and a composite image for supporting the paracentesis is presented to the doctor through the HMD. The support system is configured to generate a composite image in which an ultrasound image of an affected part of a patient, which is obtained by pressing a probe of a diagnostic ultrasound machine against the patient, is overlaid onto a camera image of the doctor's field of view taken by a video camera attached to the HMD.

In the support system according to Patent Literature 1, the ultrasound image is superimposed onto a predetermined region near the front end of the probe in the camera image, in correspondence with the position and the attitude of the probe. At this time, by using the video camera to capture a probe marker, that is, an optical marker attached to the probe, the relative position and attitude between the video camera and the probe marker are computed from the recognition state of the probe marker in the camera image. In addition, a peripheral marker, which is a different optical marker attached to a part of the body surface of the patient, is also captured by the video camera at the same time as the probe marker. With this arrangement, the relative positional and attitudinal relationship between the peripheral marker that remains fixed in place and the probe marker that moves with the probe can be detected at all times, and even if the video camera moves together with the doctor, three-dimensional position information about the probe in a global coordinate system defined with reference to a specific peripheral marker can be acquired, and an ultrasound image corresponding to the three-dimensional position information in the global coordinate system can be superimposed onto a predetermined region in the camera image.

Meanwhile, in the support system of Patent Literature 1, if the peripheral marker is not captured together with the probe marker at the same time by the video camera, the three-dimensional position of the probe in the global coordinate system cannot be computed, and the superimposed image can no longer be superimposed onto the predetermined region in the camera image. Consequently, to avoid such a situation, it is necessary to place a large number of peripheral markers in places throughout the real space so that no matter where the probe moves, at least one of the immovable peripheral markers is captured inside the camera image that captures the probe. In this case, preliminary work of capturing all of the peripheral markers fixed in place with the video camera to specify the relative positional and attitudinal relationships between each peripheral marker is necessary.

To reduce this preliminary work, the inventors previously have proposed a system that mainly uses the optical marker, complements three-dimensional position information based on a current camera image captured by a single camera with three-dimensional position information from a camera image acquired by another camera, and thereby is capable of detecting three-dimensional position information in the global coordinate system of each optical marker existing in a real space easily and precisely (see Patent Literature 2).

CITATION LIST

Patent Literature

Patent Literature 1: Japanese Patent No. 5410629
Patent Literature 2: Japanese Patent No. 6095032

SUMMARY OF INVENTION

Technical Problem

Each of the systems proposed in Patent Literature 1 and Patent Literature 2 presupposes that each optical marker needed to acquire three-dimensional position information is recognized accurately. However, in the support system according to Patent Literature 1, the recognition state of the probe marker attached to the probe may be degraded depending on the direction of the probe with respect to the video camera, and false recognition or the like may occur. As a result, the position of the ultrasound image superimposed onto the camera image may become shifted from the desired region. Also, if the probe marker leaves the field of view of the video camera, the three-dimensional position information becomes undetectable, and the superimposed image can no longer be superimposed onto the camera image. Furthermore, in each of the systems proposed in Patent Literature 1 and Patent Literature 2, if the patient moves unexpectedly and the peripheral marker that is presumed to be in a stationary state moves unintentionally, the three-dimensional positional coordinates of the peripheral marker that act as a reference when computing the global coordinate system are shifted from the initial setting, and the superimposed image can no longer be superimposed onto the desired region of the camera image.

The present invention has been proposed in light of such issues, and an object thereof is to provide a composite image generation system that contributes to superimposing a superimposed image onto a desired region inside an image of a real space acquired by a camera, even when the detection precision of position information based on an optical marker is degraded.

Solution to Problem

To achieve the above object, the present invention adopts a configuration of a composite image generation system comprising: a position information detection device that detects position information about a predetermined spot in a real space; and a processing device that generates a composite image in which a separately acquired superimposed image is overlaid onto a desired region in a camera image of the real space captured by a movably placed camera, based on the position information detected by the position information detection device, wherein the position information detection device comprises an optical tracking means that detects the position information by using the camera image, and a non-optical tracking means that detects the position information without using the camera, the optical tracking means comprises a moving optical marker that is affixed to a moving member that specifies the desired region while moving inside the real space according to any operations by a user, the moving optical marker being configured to move as one with the moving member, and an optical marker detection unit that detects position information about the moving optical marker by recognizing an image state of the moving optical marker captured by the camera, the non-optical tracking means comprises a non-optical marker affixed to the moving member, and a non-optical marker detection unit that detects position information about the non-optical marker, the processing device includes a position information specifying means that adjusts detection results from the optical tracking means and the non-optical tracking means to specify position information about the moving member used when superimposing the superimposed image onto the desired region, and the position information specifying means comprises a recognition state determination unit that determines a recognition state of the moving optical marker by the camera, a used information selection unit that selects which position information to use from among the detection results from the optical tracking means and the non-optical tracking means according to the recognition state of the moving optical marker, and an output position information decision unit that decides output position information necessary to generate the composite image according to the position information selected by the used information selection unit.

Additionally, the present invention adopts a configuration of a position information correction system comprising a processing device that, when generating a composite image in which a separately acquired superimposed image is overlaid onto a desired region in a camera image of a real space captured by a movably placed camera, adjusts position information plurally detected by a position information detection device for a moving member that specifies the desired region while moving in the real space according to any operations by a user, wherein the position information detection device comprises an optical tracking means that detects the position information by using the camera image, and a non-optical tracking means that detects the position information without using the camera, the optical tracking means comprises a moving optical marker that is affixed to the moving member and configured to move as one with the moving member, and an optical marker detection unit that detects position information about the moving optical marker by recognizing an image state of the moving optical marker captured by the camera, the non-optical tracking means comprises a non-optical marker affixed to the moving member, and a non-optical marker detection unit that detects position information about the non-optical marker, the processing device includes a position information specifying means that adjusts detection results from the optical tracking means and the non-optical tracking means to specify position information about the moving member, and the position information specifying means comprises a recognition state determination unit that determines a recognition state of the moving optical marker by the camera, a used information selection unit that selects which position information to use from among the detection results from the optical tracking means and the non-optical tracking means according to the recognition state of the moving optical marker, and an output position information decision unit that decides output position information necessary to generate the composite image according to the position information selected by the used information selection unit.

Note that in the specification and claims, "position information" means information that includes a position in a predetermined coordinate system and an attitude (direction) expressed by a rotational angle about each coordinate axis of the coordinate system. Consequently, "three-dimensional position information" means information containing six coordinate components, namely a position in each of three orthogonal axial directions and a rotational angle about each of the three axes.

Advantageous Effects of Invention

According to the present invention, by using appropriate position information from among the detection results provided by the optical tracking means and the non-optical tracking means according to the recognition state of the moving optical marker, position information about the moving member can be specified more accurately. In other words, even if the detection precision of the position information from the optical tracking means is lowered due to degraded recognition of the optical marker, it is possible to superimpose the superimposed image onto the desired region inside the camera image while using the detection result from the non-optical tracking means.

BRIEF DESCRIPTION OF DRAWINGS

FIG. 2 is a block diagram illustrating an overall configuration of the medical AR display system.

DESCRIPTION OF EMBODIMENT

Figure 1:
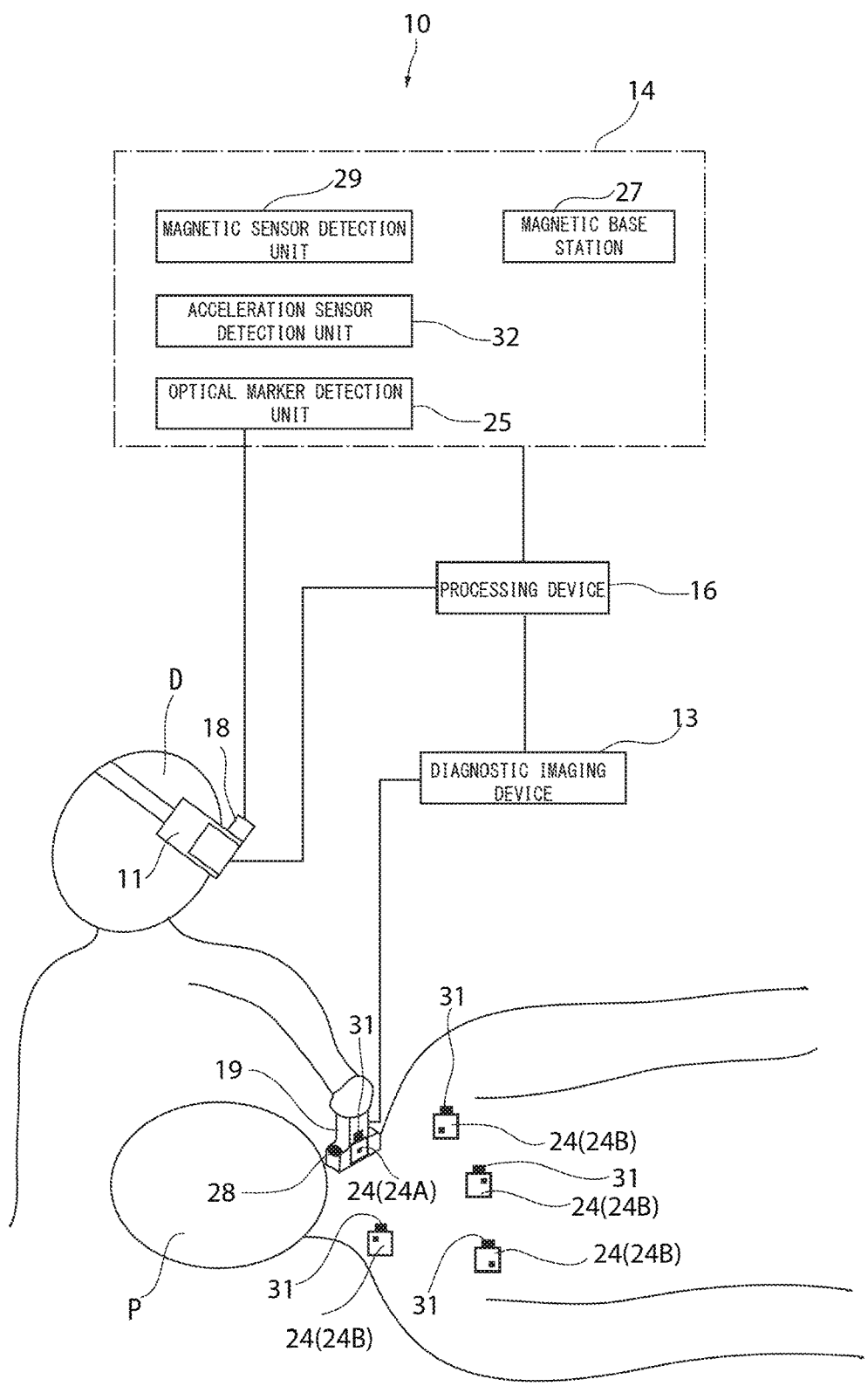
FIG. 1 is a conceptual diagram illustrating a major configuration of a medical AR display system that includes a composite image generation system according to the present invention.

Hereinafter, an embodiment of the present invention will be described with reference to the drawings.

FIG. 1 is a conceptual diagram illustrating a major configuration of a medical AR display system that includes a composite image generation system according to the present invention, and FIG. 2 is a block diagram illustrating an overall configuration of the medical AR display system. In these diagrams, a medical AR display system 10 according to the embodiment is a display system for medical support, and is an AR display system that displays, on a head-mounted display 11 (hereinafter referred to as the "HMD 11") worn by the doctor D as a user, a composite image obtained by superimposing a diagnostic image such as a corresponding ultrasound image as a superimposed image onto a partial region of an image of a real space of a patient P (primarily an affected part of the patient P) existing in the visual field of the doctor D.

The medical AR display system 10 is provided with the HMD 11 that acts as an image display device worn on the head of the doctor D, a diagnostic imaging device 13 that acquires a diagnostic image of an affected part or the like of the patient P, a position information detection device 14 that detects three-dimensional position information of a predetermined spot in the real space, and a processing device 16 that generates the composite image based on a detection result from the position information detection device 14 and presents the composite image on the HMD 11. Note that the position information detection device 14 and the processing device 16 form a composite image generation system that generates the composite image.

The device used as the HMD 11 is of the video see-through type having an attached video camera 18 that captures a camera image of the real space to be the background of the composite image, and the composite image obtained by overlaying a superimposed image onto the camera image is displayed in front of the eyes of the doctor D.

The video camera 18 is disposed to move as one with the head of the doctor D, such that the doctor D wearing the HMD 11 can acquire a camera image of substantially the same space as in the case where he or she actually looks directly at the real space in front of his or her eyes. Consequently, the doctor D is able to see the state of the patient P and the affected part existing in front of the doctor's eyes through the camera image displayed on a display of the HMD 11. Note that in the present invention, any of various types of cameras may be adopted insofar as the camera image is acquirable.

A two-dimensional diagnostic ultrasound machine is applied as the diagnostic imaging device 13. In the two-dimensional diagnostic ultrasound machine, beam scanning by a probe 19 (see FIG. 1) is used to generate an ultrasound image such as a two-dimensional tomographic image in the same section as the beam scanning plane. Also provided is a function that makes it possible to generate a stereoscopic image of objects such as organs inside the body within a predetermined range of the affected part, the stereoscopic image being generated by performing beam scanning in the predetermined range of the affected part and using the detection results described later of three-dimensional position information in the same coordinate system as the probe 19 during the beam scanning. A diagnostic image such as the ultrasound image and stereoscopic image above can be viewed by the doctor D through the HMD 11 by being stereoscopically overlaid as a superimposed image onto a desired region of the camera image of the real space. Here, the desired region of the camera image where the superimposed image is overlaid is taken to be a region near the front-end position of the probe 19 in the camera image, and the superimposed image is displayed in a direction corresponding to the direction of the probe 19 according to processing described later by the processing device 16. Consequently, the probe 19 is also configured as a moving member that specifies the desired region while moving inside the real space in accordance with any operations by the doctor D.

However, the moving member in the present invention is not limited to the probe 19, and any of various types of operating members, gripping members, or the like may also be adopted as the moving member insofar as the desired region can be specified while moving inside the real space in accordance with operations by the user.

Additionally, the diagnostic imaging device 13 is not limited to the diagnostic ultrasound machine of the present embodiment, and another diagnostic imaging device such as a CT scanner or an MRI scanner may also be applied as the diagnostic imaging device 13.

As illustrated in FIG. 2, the position information detection device 14 includes optical tracking means 21 that detects three-dimensional position information at a predetermined spot in the real space by utilizing the camera image from the video camera 18, and non-optical tracking means 22 that detects three-dimensional position information at a predetermined spot in the real space without utilizing the camera image.

The optical tracking means 21 is an optical tracking system that includes optical markers 24 respectively installed at a plurality of predetermined spots in a real space, and an optical marker detection unit 25 that recognizes the image state of each optical marker 24 in the camera image captured by the video camera 18, and thereby detects three-dimensional position information for the optical marker 24 at each installed spot in a local coordinate system defined by three orthogonal axes that take the center of the video camera 18 as the origin. In other words, through the optical markers 24, the optical tracking means 21 is capable of detecting three-dimensional position information about the spot where each optical marker 24 is installed.

As illustrated in FIG. 1, the optical markers 24 include a probe marker 24A affixed to a part of the probe 19, and peripheral markers 24B affixed to a plurality of locations on a part of the body surface of the patient P lying face-up. Note that the surface of each optical marker 24 has a predetermined marking, optical markers 24 with a plurality of patterns having different markings are prepared, and an optical marker 24 with a different marking is used at each installed spot.

The probe marker 24A functions as a moving optical marker capable of moving as one with the probe 19, while the peripheral markers 24B function as fixed optical markers presumably disposed in a stationary state.

In the optical marker detection unit 25, when the optical markers 24 appear in the camera image captured by the video camera 18, the following process using known approaches is performed through image recognition of the optical markers 24. Specifically, because the marking, shape, and size of each optical marker 24 is known, an ID expressing where an optical marker 24 is disposed is specified from the marking of the optical marker 24 in the camera image, while in addition, the position and direction of the optical marker 24 are computed from the size and shape of the optical marker 24 in the camera image. Here, the position and direction of an optical marker 24 are acquired as three-dimensional position information in an HMD coordinate system whose origin is the center of the video camera 18 capturing an image of the optical marker 24.

Consequently, in the optical marker detection unit 25, three-dimensional position information in the HMD coordinate system is continually acquired for each optical marker 24 captured by the video camera 18 of the HMD 11 worn by the doctor D. The HMD coordinate system is treated as a local coordinate system that moves in association with the movement of the head of the doctor D wearing the HMD 11.

The non-optical tracking means 22 includes a magnetic tracking system 22A that uses magnetic data to compute three-dimensional position information, and an acceleration tracking system 22B that uses acceleration data to compute three-dimensional position information.

The magnetic tracking system 22A includes a magnetic base station 27 that generates magnetic fields of various strengths in various directions in the real space, a magnetic sensor 28 that acts as a non-optical marker that detects the magnitude of the magnetism from the magnetic base station 27, and a magnetic sensor detection unit 29 that acts as a non-optical marker detection unit that detects three-dimensional position information about the spot where the magnetic sensor 28 is installed from the magnetic detection state of the magnetic sensor 28. In other words, through the magnetic sensor 28, the magnetic tracking system 22A is capable of detecting three-dimensional position information about the spot where the magnetic sensor 28 is installed.

The magnetic sensor 28 is affixed to a predetermined spot on the continually moving probe 19, and is attached to be immovable and also non-rotatable relative to the probe marker 24A affixed to the probe 19.

In the magnetic sensor detection unit 29, by using the magnetic sensor 28 to sense the direction and strength of the magnetic field generated by the magnetic base station 27, three-dimensional position information in a magnetic coordinate system defined by three orthogonal axes that take a predetermined spot on the magnetic base station 27 as the origin is continually acquired for the probe 19 to which the magnetic sensor 28 is attached. Because the magnetic base station 27 exists in a single place and is also fixed in place, the magnetic coordinate system is treated as a local coordinate system that is fixed in an immovable and non-rotatable way.

The acceleration tracking system 22B includes an acceleration sensor 31 that functions as a non-optical marker affixed to a predetermined spot, and an acceleration sensor detection unit 32 that acts as a non-optical marker detection unit that computes three-dimensional position information about the predetermined spot where the acceleration sensor 31 is attached from a measurement value by the acceleration sensor 31.

The acceleration sensor 31 is affixed to each of the optical markers 24, and is disposed to be immovable and also non-rotatable relative to each optical marker 24 to which the acceleration sensor 31 is attached. The acceleration sensor 31 includes a six-axis acceleration sensor capable of measuring the acceleration in each of three orthogonal axis directions and also the angular velocity about each axis.

The acceleration sensor detection unit 32 is configured to acquire the change over time in the acceleration and the angular velocity from an initial position, and thereby compute three-dimensional position information about the spot where the acceleration sensor 31 is installed at the current point in time in an acceleration coordinate system, which is a local coordinate system that takes the initial position as the origin.

Note that the non-optical tracking means 22 may be configured using any type of sensor that specifies three-dimensional position information in a local coordinate system that takes a preset reference point as the origin for a non-optical marker by tracking the non-optical marker without using the video camera 18.

For example, although omitted from the drawings, an ultrasound tracking system that uses ultrasound may be adopted as another non-optical tracking means 22, and may be used instead of the magnetic tracking system 22A and acceleration tracking system 22B described above or together with the tracking systems 22A and 22B. In the ultrasound tracking system, an emitter that emits ultrasonic waves of various frequencies and intensities is affixed to a predetermined spot in the real space as an ultrasound marker that acts as a non-optical marker, and the frequencies and intensities of the ultrasonic waves are measured by a plurality of microphones installed in an ultrasound receiver station. Additionally, by using the principle of triangulation, three-dimensional position information in an ultrasound coordinate system defined by three orthogonal axes that take a predetermined point in the ultrasound receiver station as the origin is continually acquired for the spot where the ultrasound marker is installed. Like the magnetic coordinate system, the ultrasound coordinate system is also treated as a local coordinate system that is fixed in place by the stationary positioning of the ultrasound receiver station. Even in the case where the ultrasound tracking system is adopted, the process described later is performed similarly on the above three-dimensional position information acquired by the non-optical tracking means 22 based on the acquired three-dimensional position information.

Note that, in the following description, three-dimensional position information in the HMD coordinate system, the magnetic coordinate system, and the acceleration coordinate system that is local coordinate systems is referred to as "local position information" where appropriate. Also, three-dimensional position information in a global coordinate system defined by three orthogonal axes that take a preset fixed point set in the real space as the origin is referred to as "global position information" where appropriate.

The processing device 16 includes a computer containing a computational processing component such as a CPU, storage components such as memory and a hard disk, and the like, and a program for causing the computer to function as each means and each unit described hereinafter is installed in the computer.

As illustrated in FIG. 2, the processing device 16 is provided with a position information specifying means 35 that adjusts detection results from the optical tracking means 21 and the non-optical tracking means 22 and specifies three-dimensional position information about the probe 19 when superimposing a diagnostic image from the diagnostic imaging device 13 onto a desired region of the camera image of the real space, an image capturing means 36 that captures various types of image data obtained by the diagnostic imaging device 13 and the video camera 18, and a composite image generating means 37 that generates a composite image presented to the HMD 11 of each doctor D based on the three-dimensional position information computed by the position information specifying means 35.

The position information specifying means 35 includes a global position information conversion function 39 that arithmetically converts local position information detected by the position information detection device 14 into global position information, a moving position information adjustment function 40 forming a position information correction system that adjusts the global position information about the probe 19 computed by the global position information conversion function 39, and an initial condition reset function 41 forming an initial condition resetting system that resets a predetermined initial condition that acts as a reference when computing the global position information.

The global position information conversion function 39 is provided with an initial setting unit 43 that sets the global coordinate system in a stationary state in which the probe 19 and the patient P are still, and a coordinate conversion unit 44 that converts three-dimensional position information about the probe 19 in a local coordinate system to the global coordinate system.

In the initial setting unit 43, an initial setting that sets the following initial condition is continually performed, and the global coordinate system is set by using a detection result from the position information detection device 14 in the initial setting.

More specifically, at this point, the probe marker 24A and the peripheral markers 24B are captured at the same time by the video camera 18 arranged in a position and a direction enabling accurate image recognition in a state in which each of the optical markers 24, the magnetic sensor 28, and the acceleration sensor 31 are still. At this time, one of the peripheral markers 24B, such as the peripheral marker 24B closest to the probe marker 24A, for example, is specified as a reference peripheral marker 24B, and a global coordinate system whose origin is at the center of the reference peripheral marker 24B is set.

In the coordinate conversion unit 44, after the initial setting is performed by the initial setting unit 43, the detection values in each local coordinate system acquired by the position information detection device 14, namely the three-dimensional position information acquired by the optical markers 24, the magnetic sensor 28, and the acceleration sensor 31, are each converted to the global coordinate system arithmetically.

Here, the local position information about each optical marker 24 is converted into global position information as follows.

Namely, the relative positional and attitudinal relationship of the peripheral markers 24B attached to the patient P when the patient P is still is treated as invariant. For this reason, when the patient P is still and the peripheral markers 24B are in a stationary state and not moving, the three-dimensional position information in the HMD coordinate system for each peripheral marker 24B is invariant, and the three-dimensional position information for the other peripheral markers 24B in the global coordinate system that treats the reference peripheral marker 24B as the origin is also computed as a fixed value.

On the other hand, the local position information about the probe marker 24A detected by the position information detection device 14 continually changes due to the doctor D operating the probe 19. Meanwhile, if the peripheral markers 24B are in the stationary state, because the positional and attitudinal relationship relative to the peripheral markers 24B is invariant, if at least one of the peripheral markers 24B is captured by the video camera 18 at the same time as the probe marker 24A, global position information about the probe marker 24A is computed from the detection results in the HMD coordinate system. Note that when the detection state of one of the peripheral markers 24B changes from the initial setting, such as when the patient P moves from the stationary state, as described later, the global position information about the peripheral markers 24B is reset by the initial condition reset function 41, and the initial condition is newly set by the initial setting unit 43.

Also, the local position information acquired by the magnetic sensor 28 is converted into global position information as follows. Specifically, the magnetic sensor 28 is attached to the probe 19 together with the probe marker 24A in an immovable and non-rotatable way. Consequently, the relative relationship between the magnetic coordinate system and the global coordinate system is specified from the three-dimensional position information about the probe 19 in the magnetic coordinate system in the initial setting, based on the relative positional and attitudinal relationship between the probe marker 24A and the reference peripheral marker 24B. Additionally, from the relative relationship, detection values in the magnetic coordinate system by the magnetic sensor 28 are converted into components of the unified global coordinate system.

Furthermore, the global position information for the installation spot is obtained from the detection results by the acceleration sensor 31 as follows. Specifically, when setting the initial condition, global position information in the initial state for each of the optical markers 24 integrally attached to the acceleration sensor 31 is specified as described earlier. After that, the change over time in the acceleration in each of the three orthogonal axis directions and the angular velocity about each of the three axes is acquired by the acceleration sensor detection unit 32, and from the acquired values, the amount of movement and the amount of rotation at the spot where the acceleration sensor 31 is installed are computed. Thereafter, by adding the amount of movement and the amount of rotation to the global position information in the initial state, global position information about the spot where the acceleration sensor 31 is installed is obtained.

The moving position information adjustment function 40 is provided with a recognition state determination unit 46 that determines the recognition state of each probe marker 24A by the video camera 18, a used information selection unit 47 that selects which detection result to use from among the global position information from the probe marker 24A, the magnetic sensor 28, and the acceleration sensor 31 computed by the global position information conversion function 39 according to the recognition state of the probe marker 24A, and an output position information decision unit 48 that decides output position information for the probe 19 used by the composite image generating means 37 according to the selected three-dimensional position information by the used information selection unit 47.

In the recognition state determination unit 46, the recognition state of the probe marker 24A is determined based on the relative distance and the relative angle between the video camera 18 and the probe marker 24A at the current point in time. In other words, first, the relative distance and the relative angle at the current point in time are obtained arithmetically from the local position information for the probe marker 24A detected by the optical marker detection unit 25. Here, a stability database 49 containing information such as a table or a formula expressing the relationship between the relative distance and the relative angle and the recognition stability for each size of the probe marker 24A to be used is stored in advance. The recognition stability corresponding to the relative distance and the relative angle at the current point in time is specified from the stability database 49. The relationship stored in the stability database 49 is set according to experimental results acquired in advance, and the recognition stability becomes unstable as the relative distance becomes longer or the relative angle becomes larger. Note that the recognition stability in the present embodiment is taken to be either a stable state for which the recognition rate of the probe marker 24A is in a high range or an unstable state for which the recognition rate is in a low range, but the present invention is not limited thereto, and the recognition stability may also be quantified or divided into even more levels.

In other words, in the recognition state determination unit 46, when the probe marker 24A is recognized by the video camera 18, the recognition stability of the probe marker 24A is determined to be in either the stable state or the unstable state according to the relative distance and the relative angle between the video camera 18 and the probe marker 24A, based on the stability database 49. On the other hand, when the probe marker 24A is not recognized by the video camera 18, the probe marker 24A is determined to be in an unrecognizable state.

The used information selection unit 47 decides which of the global position information obtained by the global position information conversion function 39 based on the detection results acquired by the probe marker 24A, the magnetic sensor 28, and the acceleration sensor 31 to use as follows.

Specifically, at this point, if the probe marker 24A is recognized inside the field of view of the video camera 18 and is in a first recognition state determined to be a stable state by the recognition state determination unit 46, the used information selection unit 47 decides to use only the global position information acquired by the probe marker 24A.

Also, if the probe marker 24A is recognized inside the field of view of the video camera 18 but is in a second recognition state determined to be an unstable state by the recognition state determination unit 46, the used information selection unit 47 decides to use the three types of global position information acquired by the probe marker 24A, the magnetic sensor 28, and the acceleration sensor 31.

Furthermore, if the probe marker 24A is not recognized inside the field of view of the video camera 18 and is in a third recognition state determined to be an unrecognizable state, the used information selection unit 47 decides to use the two types of global position information acquired by the magnetic sensor 28 and the acceleration sensor 31.

In the output position information decision unit 48, the output position information is decided using different position information depending on the above first to third recognition states as follows.

Specifically, if the probe marker 24A is in the first recognition state determined to be a stable state, the global position information about the probe marker 24A is treated directly as the output position information.

Also, if the probe marker 24A is in the second recognition state determined to be an unstable state, the three types of global position information acquired by the probe marker 24A, the magnetic sensor 28, and the acceleration sensor 31 are used, and a corrected value considering error information about these types of global position information is decided as the output position information. The error information used at this point is measurement error for each of the optical markers 24, the magnetic sensor 28, and the acceleration sensor 31, and the measurement error is specified by using a preset error database 50. In other words, with regard to the measurement error of the position and the angle of the optical markers 24, predetermined values depending on the distance from the video camera 18 are stored in the error database 50. Also, with regard to the measurement error of the position and the angle in the magnetic sensor 28, predetermined values depending on the distance from the magnetic base station 27 are stored in the error database 50. Furthermore, with regard to the measurement error of the position and the angle in the acceleration sensor 31, predetermined values specified for each product are stored in the error database 50.

Accordingly, in the case of the second recognition state, first, the measurement error corresponding to each distance is specified according to the error database 50 from the detection results acquired by the probe marker 24A and the magnetic sensor 28. Additionally, the average value of the respective global position information accounting for the measurement error is treated as the output position information. In other words, at this point, the measurement error for the probe marker 24A, the magnetic sensor 28, and the acceleration sensor 31 is compared, and weighting values that take larger values in order of the smallest measurement error are respectively set. Additionally, by adding together the global position information obtained by the probe marker 24A, the magnetic sensor 28, and the acceleration sensor 31 multiplied by their corresponding weighting values and dividing the total value by the sum of the weighting values, an average value that acts as the corrected value of the three-dimensional position information is obtained. Note that the arithmetic approach at this point is not limited to the above, and any of various arithmetic approaches may be adopted insofar as the output position information is obtained by combining and correcting the different types of global position information acquired by the probe marker 24A, the magnetic sensor 28, and the acceleration sensor 31 while also prioritizing the global position information having a small value of measurement error.

In addition, if the probe marker 24A is in the third recognition state determined to be an unrecognizable state, the output position information is obtained from the two types of global position information from the magnetic sensor 28 and the acceleration sensor 31 according to an approach similar to the case of the second recognition state, except that the global position information acquired by the probe marker 24A is not used.

The initial condition reset function 41 decides whether or not to reset the three-dimensional position information for each peripheral marker 24B specified by the initial setting in the initial setting unit 43, based on the recognition state of each peripheral marker 24B presumed to be in the stationary state and the detection results from the acceleration sensor 31 integrally attached to each peripheral marker 24B. In the case of deciding to perform a reset, the initial setting is set again by the initial setting unit 43, whereas in the case of not deciding to perform a reset, the process thereafter continues.

First, in the case of a first state change in which one of the peripheral markers 24B inside the field of view of the video camera 18 moves and a moving state is detected by the acceleration sensor 31 provided in that peripheral marker 24B, the global position information for all of the peripheral markers 24B is reset, regardless of whether there is a change in the recognition state of each peripheral marker 24B. In this case, the acceleration sensor 31 functions as a movement detection sensor capable of detecting the moving state of the peripheral marker 24B.

Also, in the case of the second state change in which the detection result from the optical marker detection unit 25 changes within a predetermined amount of time according to a result such as a false recognition due to an increase in the angle relative to the video camera 18 or the like for one of the peripheral markers 24B inside the field of view of the video camera 18, the recognition state of the peripheral marker 24B is considered to have changed and the global position information for all of the peripheral markers 24B is reset, even if the moving state has not been detected by the acceleration sensor 31.

Furthermore, in the case of the third state change in which the moving state is detected by the acceleration sensor 31 provided in one of the peripheral markers 24B outside the field of view of the video camera 18 and not recognized in the camera image, the global position information for the other peripheral markers 24B inside the field of view of the video camera 18 is reset.

The global position information for the peripheral markers 24B is not reset as long as the first to third state changes do not apply. Consequently, for example, in the case where the moving state of the peripheral markers 24B is not detected by the acceleration sensor 31, the global position information for the peripheral markers 24B is not reset, even if a predetermined peripheral marker 24B exists outside the field of view of the video camera 18 and is not recognized in the camera image.

The composite image generating means 37 generates a composite image from each image captured by the image capturing means 36 and output position information about the probe 19 decided by the position information specifying means 35, such that a superimposed image is displayed near the position of the front end and facing the corresponding direction of the probe 19 in the camera image. Specifically, the position and the attitude of the probe 19 in the camera image to be a background image are specified based on the output position information about the probe 19, and a diagnostic image of the affected part at the corresponding position is superimposed on the front-end portion of the probe 19 in the camera image and in a direction corresponding to the attitude of the probe 19.

Note that although the present embodiment illustrates and describes an example of applying the composite image generation system according to the present invention to the AR display system 10 used in the medical field, the present invention is not limited thereto, and a similar configuration is applicable to systems in general that generate a composite image by superimposing a superimposed image acquired separately onto a desired region in a camera image specified by a moving member that moves inside a predetermined space, the superimposed image being superimposed in correspondence with the position and the attitude of the moving member.

In addition, the configuration of each component of the devices in the present invention is not limited to the illustrated configuration examples, and various modifications are possible insofar as substantially the same effects are exhibited.

INDUSTRIAL APPLICABILITY

The present invention is usable as a system that generates a composite image by superimposing a superimposed image acquired separately onto a desired region in a camera image specified by a moving member that moves inside a predetermined space, the superimposed image being superimposed in correspondence with the position and the attitude of the moving member.

REFERENCE SIGNS LIST

- 10 medical AR display system
- 14 position information detection device (composite image generation system)
- 16 processing device (composite image generation system)
- 18 video camera (camera)
- 19 probe (moving member)
- 21 optical tracking means
- 22 non-optical tracking means
- 22A magnetic tracking system
- 22B acceleration tracking system
- 24 optical marker
- 24A probe marker (moving optical marker)
- 24B peripheral marker (fixed optical marker)
- 25 optical marker detection unit
- 28 magnetic sensor (non-optical marker)
- 29 magnetic sensor detection unit (non-optical marker detection unit)
- 31 acceleration sensor (non-optical marker, movement detection sensor)
- 32 acceleration sensor detection unit (non-optical marker detection unit)
- 35 position information specifying means
- 40 moving position information adjustment function (position information correction system)
- 41 initial condition reset function (initial condition resetting system)
- 46 recognition state determination unit
- 47 used information selection unit
- 48 output position information decision unit
- 49 stability database
- 50 error database
- D doctor (user)

The invention claimed is:

1. A composite image generation system comprising: a position information detection device that detects position information about a predetermined spot in a real space; and a processing device that generates a composite image in which a separately acquired superimposed image is overlaid onto a desired region in a camera image of the real space captured by a movably placed camera, based on the position information detected by the position information detection device, wherein the position information detection device comprises an optical tracking means that detects the position information by using the camera image, and a non-optical tracking means that detects the position information without using the camera, the optical tracking means comprises a moving optical marker that is affixed to a moving member that specifies the desired region while moving inside the real space according to any operations by a user, the moving optical marker being configured to move as one with the moving member, and an optical marker detection unit that detects position information about the moving optical marker by recognizing an image state of the moving optical marker captured by the camera, the non-optical tracking means comprises a non-optical marker affixed to the moving member, and a non-optical marker detection unit that detects position information about the non-optical marker, the processing device includes a position information specifying means that adjusts detection results from the optical tracking means and the non-optical tracking means to specify position information about the moving member used when superimposing the superimposed image onto the desired region, and the position information specifying means comprises a recognition state determination unit that determines a recognition state of the moving optical marker by the camera, a used information selection unit that selects which position information to use from among the detection results from the optical tracking means and the non-optical tracking means according to the recognition state of the moving optical marker, and an output position information decision unit that decides output position information necessary to generate the composite image according to the position information selected by the used information selection unit.

2. The composite image generation system according to claim 1, wherein in the recognition state determination unit, when the moving optical marker is recognized by the camera, the recognition state is determined based on a relative distance and a relative angle between the camera and the moving optical marker computed from a detection result from the optical marker detection unit.

3. The composite image generation system according to claim 1, wherein in the recognition state determination unit, when the moving optical marker is recognized by the camera, the recognition state is determined to be either a stable state for which a recognition rate of the moving optical marker is high or an unstable state for which the recognition rate is low from a relative distance and a relative angle between the camera and the moving optical marker computed from a detection result from the optical marker detection unit according to a stability database stored in advance, whereas when the moving optical marker is not recognized, the recognition state is determined to be an unrecognizable state.

4. The composite image generation system according to claim 3, wherein in the used information selection unit, when in the stable state, the position information detected by the optical tracking means is selected, while when in the unstable state, the position information detected by the optical tracking means and the position information detected by the non-optical tracking means are selected, and when in the unrecognizable state, the position information detected by the non-optical tracking means is selected.

5. The composite image generation system according to claim 4, wherein in the output position information decision unit, when in the unstable state, an average value of the position information from the optical tracking means and the position information from the non-optical tracking means with measurement error accounted for is treated as the output position information.

6. The composite image generation system according to claim 5, wherein
the non-optical tracking means comprises a magnetic tracking system that obtains the position information by using magnetic data acquired by a magnetic sensor that functions as the non-optical marker, and an acceleration tracking system that obtains the position information by using acceleration data acquired by an acceleration sensor that functions as the non-optical marker, and
in the output position information decision unit, when in the unrecognizable state, an average value of the position information from the magnetic sensor and the position information from the acceleration sensor with measurement error accounted for is treated as the output position information.

7. The composite image generation system according to claim 6, wherein in the output position information decision unit, a distance from the camera to the moving optical marker and a distance from the magnetic sensor to a detection point by the magnetic sensor are computed from detection results from the position information detection device, and the measurement error is specified according to an error database stored in advance in which each distance is associated with the measurement error.

8. The composite image generation system according to claim 7, wherein in the output position information decision unit, a weighting value corresponding to the measurement error is decided, each piece of position information is multiplied by the corresponding weighting value, and a total value obtained by adding together the multiplied values is divided by a sum of the weighting values to compute the average value.

9. A position information correction system comprising a processing device that, when generating a composite image in which a separately acquired superimposed image is overlaid onto a desired region in a camera image of a real space captured by a movably placed camera, adjusts position information plurally detected by a position information detection device for a moving member that specifies the desired region while moving in the real space according to any operations by a user, wherein
the position information detection device comprises an optical tracking means that detects the position information by using the camera image, and a non-optical tracking means that detects the position information without using the camera,
the optical tracking means comprises a moving optical marker that is affixed to the moving member and configured to move as one with the moving member, and an optical marker detection unit that detects position information about the moving optical marker by recognizing an image state of the moving optical marker captured by the camera,
the non-optical tracking means comprises a non-optical marker affixed to the moving member, and a non-optical marker detection unit that detects position information about the non-optical marker,
the processing device includes a position information specifying means that adjusts detection results from the optical tracking means and the non-optical tracking means to specify position information about the moving member, and
the position information specifying means comprises a recognition state determination unit that determines a recognition state of the moving optical marker by the camera, a used information selection unit that selects which position information to use from among the detection results from the optical tracking means and the non-optical tracking means according to the recognition state of the moving optical marker, and an output position information decision unit that decides output position information necessary to generate the composite image according to the position information selected by the used information selection unit.

* * * * *